(12) United States Patent
Thakur et al.

(10) Patent No.: US 8,750,982 B2
(45) Date of Patent: Jun. 10, 2014

(54) PHYSIOLOGICAL STATUS INDICATOR APPARATUS AND METHOD

(71) Applicant: Cardiac Pacemakers, Inc., St. Paul, MN (US)

(72) Inventors: Pramodsingh Hirasingh Thakur, White Bear Lake, MN (US); John D. Hatlestad, Maplewood, MN (US); Ramesh Wariar, Blaine, MN (US); Viktoria A. Averina, Roseville, MN (US); Lynne E. Swanson, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/725,675

(22) Filed: Dec. 21, 2012

(65) Prior Publication Data

US 2013/0165755 A1  Jun. 27, 2013

Related U.S. Application Data

(60) Provisional application No. 61/580,099, filed on Dec. 23, 2011.

(51) Int. Cl.
*A61B 5/053* (2006.01)
(52) U.S. Cl.
USPC .......................................... 600/547; 600/506
(58) Field of Classification Search
USPC ................................................. 600/506, 547
See application file for complete search history.

(56) References Cited

U.S. PATENT DOCUMENTS 7,010,347 B2    3/2006  Schecter
(Continued)

FOREIGN PATENT DOCUMENTS

| EP | 2143467 A1 | 1/2010 |
|---|---|---|
| WO | WO-2010051123 A1 | 5/2010 |
| WO | WO-2010129095 A2 | 11/2010 |
| WO | WO-2013096905 A1 | 6/2013 |

OTHER PUBLICATIONS

Hettrick, Douglas A, et al., "Human Feasibility study of Hemodynamic Monitoring via Continuous Intrathoracic Impedance monitoring", 31st Annual International Conference of the IEEE EMBS, Minneapolis, Minnesota, USA, Sep. 2-6, 2009, 4611-4614.

(Continued)

*Primary Examiner* — Michael Kahelin
(74) *Attorney, Agent, or Firm* — Schwegman, Lundberg & Woessner, P.A.

(57) ABSTRACT

A processor circuit can be configured to obtain a first multi-dimensional vector. The first multidimensional vector can include dimensions corresponding to respective first conductivity characteristics obtained from different implantable electrode configurations associated with a subject. The processor circuit can also be configured to obtain a second multidimensional vector or vector space. The second multidimensional vector or vector space can include dimensions corresponding to respective second conductivity characteristics obtained from such different electrode configurations associated with the same or a different subject. The processor circuit can also provide a physiological status indicator that can be obtained at least in part by performing a vector comparison of the first multidimensional vector to the second multidimensional vector space or vector.

20 Claims, 9 Drawing Sheets

(56) References Cited

U.S. PATENT DOCUMENTS

| | | | |
|---|---|---|---|
| 7,047,083 B2 | 5/2006 | Gunderson et al. | |
| 7,149,573 B2 | 12/2006 | Wang | |
| 7,474,918 B2 | 1/2009 | Frantz et al. | |
| 7,488,290 B1 | 2/2009 | Stahmann et al. | |
| 7,574,255 B1 | 8/2009 | Min | |
| 7,627,367 B2 | 12/2009 | Warren et al. | |
| 7,672,718 B2 | 3/2010 | Stahmann et al. | |
| 7,826,896 B2 | 11/2010 | Wang | |
| 7,879,115 B2 | 2/2011 | Stahmann | |
| 7,979,115 B2 | 7/2011 | Stahmann et al. | |
| 2001/0018608 A1 | 8/2001 | Panescu et al. | |
| 2007/0038078 A1 | 2/2007 | Osadchy | |
| 2007/0043394 A1 | 2/2007 | Zhang et al. | |
| 2007/0142733 A1 | 6/2007 | Hatlestad et al. | |
| 2008/0108907 A1* | 5/2008 | Stahmann et al. | 600/529 |
| 2009/0069708 A1 | 3/2009 | Hatlestad et al. | |
| 2010/0004712 A1 | 1/2010 | Zhao et al. | |
| 2010/0056884 A1 | 3/2010 | Kwok et al. | |
| 2010/0113962 A1 | 5/2010 | Hettrick et al. | |
| 2010/0121397 A1 | 5/2010 | Cholette | |
| 2011/0098771 A1 | 4/2011 | Thakur et al. | |
| 2011/0125049 A1 | 5/2011 | Nabutovsky et al. | |
| 2011/0125207 A1 | 5/2011 | Nabutovsky et al. | |
| 2011/0144526 A1 | 6/2011 | Stahmann et al. | |

OTHER PUBLICATIONS

Khoury, Dirar S, et al., "Heart Failure: Resynchronization Therapy I Abstract 820: Usefulness of Monitoring Congestive Heart Failure by Multiple Bioelectric Impedance Vectors", Abstract American Heart Association; Circultion, 2008; 8:S_618, 1 pg.

Khoury, PhD, Dirar S, et al., "Ambulatory Monitoring of Congestive Heart Failure by Multiple Bioelectric Impedance Vectors", Journal of American College of Cardiology vol. 53 No. 12, (2009), 7 pgs.

Madias, John E, "Multiple Bioelectric Impedance Vectors in the Monitoring of Congestive Heart Failure", J. Am. Coll Cardiol, 2010; 55; 259, (Jan. 19, 2010), 3 pgs.

Panescu, Dorin, et al., "Usefulness of Monitoring Congestive Heart Failure by Multiple Impedance Vectors", 30th Annual International IEEE EMBS Conference, Vancouver, British Columbia, Canada, Aug. 20-24, 2008, 5668-5670.

"International Application Serial No. PCT/US2012/071481, International Search Report mailed Apr. 2, 2013", 3 pgs.

"International Application Serial No. PCT/US2012/071481, Written Opinion mailed Apr. 2, 2013", 5 pgs.

Ginks, Matthew R, et al., "Relationship between intracardiac impedance and left ventricular contractility in patients undergoing cardiac resynchronization therapy", European Society of Cariology, Europace Advance Access, (Apr. 15, 2011), 8 pgs.

\* cited by examiner

| ELECTRODE CONFIGURATIONS → | RA-Can | RV-Can | LV-Can | RA-LV-Can | RVtc | LVdp | RV-LV |
|---|---|---|---|---|---|---|---|
| VASCULAR VOL. CHANGE (10 ML/KG HETASTARCH) | −26% | −27% | −25% | −12% | −11% | −12% | −33% |
| HCT CHANGE (10%) | 4% | 3% | 3% | 7% | 5% | 2% | 2% |
| EVLW CHANGE (200 ML) | 0% | 0% | −2% | −8% | 2% | −8% | −4% |
| FLUID IN THE POCKET (100ML SALINE INJ.) | −15% | −16% | −16% | −10% | N/A | N/A | N/A |

PHYSIOLOGICAL STATUS INDICATOR APPARATUS AND METHOD

CLAIM OF PRIORITY

This application claims the benefit of priority under 35 U.S.C. §119(e) of Thakur et al., U.S. Provisional Patent Application Ser. No. 61/580,099, entitled "PHYSIOLOGICAL STATUS INDICATOR APPARATUS AND METHOD", filed on Dec. 23, 2011, which is herein incorporated by reference in its entirety.

BACKGROUND

Diagnosis of a physiological condition of a subject can include various physiological factors. Generally, impedance changes over time can be measured to monitor and identify a physiological condition. The impedance changes over time of a particular electrode configuration or a vector can have many contributing factors. These factors can contribute to impedance signal changes measured by a device. The contributing factors can include changes in lung resistivity, changes in blood resistivity, changes in heart muscle resistivity, changes in heart or lung volumes, or other physiological factors. Measuring changes in impedances can be used to indicate changes in physiological factors. However, not all of the contributing physiological impedance factors are indicative of important physiological change, which might require clinical intervention. Isolating a particular physiological factor or a combination of physiological factors that contribute to the change in impedances can be difficult.

OVERVIEW

Some patient monitoring systems such as implantable medical devices can monitor multiple physiological factors by measuring an impedance across one vector and subsequently, another impedance across another vector. Both impedances can be affected by multiple physiological factors. A change in impedance can be determined by using both impedance measurements and, in turn, a value of one of the contributing physiological impedance factors can be determined. An ability to extract clinically relevant impedance changes can improve impedance monitoring in clinical settings.

In examples, this document describes subject matter that can include an apparatus, method, or a device-readable medium that can include device readable instructions. The subject matter can include or use a processor circuit. The processor circuit can be configured to obtain a first multidimensional vector. The first multidimensional vector can include dimensions corresponding to respective first conductivity characteristics obtained from different implantable electrode configurations associated with a subject. The processor circuit can also be configured to obtain a second multidimensional vector or vector space. The second multidimensional vector or vector space can include dimensions corresponding to respective second conductivity characteristics obtained from the different electrode configurations associated with the same or a different subject.

In examples, the first conductivity characteristics can be of the same type as the second conductivity characteristics. The different electrode configurations corresponding to the respective dimensions of the first multidimensional vector can be of the same type as the different electrode configurations corresponding to the respective dimensions of the second multidimensional vector space or vector. The processor circuit can provide a physiological status indicator obtained at least in part by performing a static or dynamic vector comparison of the first multidimensional vector to the second multidimensional vector space or vector.

BRIEF DESCRIPTION OF THE FIGURES

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
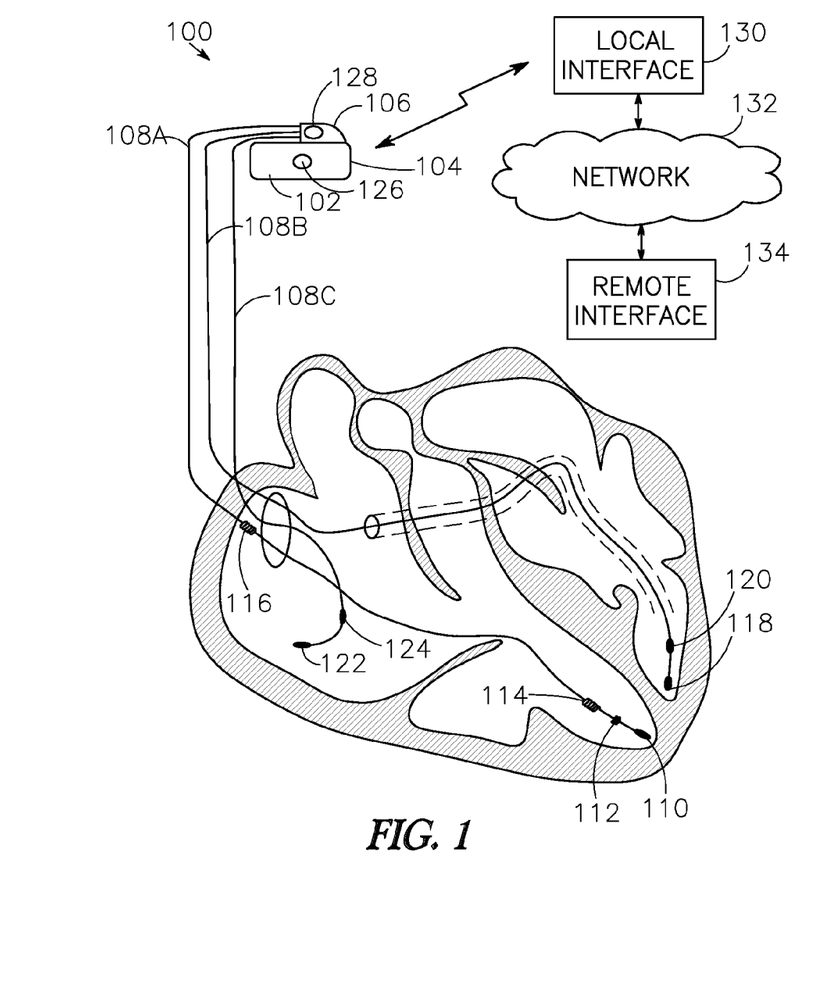
FIG. 1 illustrates, by way of an example, but not by way of limitation, an implanted Cardiac Rhythm Management (CRM) device.

FIG. 1 illustrates, by way of an example, but not by way of limitation, an implantable or other ambulatory medical device, such as a Cardiac Rhythm Management (CRM) device 100. The CRM device 100 can include an apparatus 102 that can include a hermetically-sealed housing 104 and a header 106. The header 106 can extend from the housing 104. Further, the header 106 can include one or more receptacles, such as for receiving proximal ends of leads 108A-108C. In an example, the lead 108A can include an intravascular right ventricle (RV) lead that extends from the superior vena cava (SVC) into the right atrium (RA), and then into the RV. The lead 108A can include an RV tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular coronary sinus (CS)/left ventricle (LV) lead 108B extends from the SVC into the RA through the CS into the coronary vasculature, such as near a portion of the LV.

In an example, the CS/LV lead 108B can include a distal electrode 118 and a proximal electrode 120 through which electrostimulation energies can be delivered or intrinsic electrical heart signals can be sensed. An intravascular RA lead 108C can extend from the SVC into the RA, and can include a distal electrode 122 and a proximal electrode 124. Other electrodes (e.g., a housing electrode 126 on the housing 104, a header electrode 128 on the header 106, an epicardial electrode, a subcutaneous electrode located away from the heart, or an electrode located elsewhere) or leads can be used. In an example, the CRM device 100 can be implantable and can be coupled to different implantable electrode configurations. The different implantable electrode configurations can include various combinations of sensing and stimulating pairs. For example, one electrode configuration (RA-Can) can be set up by sending a stimulating current between RA-ring electrode and the can housing and sensing the resulting voltage between RA-tip electrode and the can housing. The other configurations can include but are not limited to RV-Can (configuration utilizing electrodes on the Right Ventricular lead and active pectoral can for stimulation and sensing), LV-Can (configuration utilizing electrodes on the Left Ventricular lead and active pectoral can for stimulation and sensing), RA-LV-Can (configuration utilizing electrodes on the Right Atrial lead, Left Ventricular lead and active pectoral can for stimulation and sensing), RVtc, LVdp, RV-LV (configuration utilizing electrodes on Right Ventricular lead and Left Ventricular lead for sensing and stimulating), and the like. In an example, the CRM device 100 is not implantable.

The CRM device 100 can communicate, wirelessly or through a wired connection such as by using a tether, unidirectionally or bidirectionally with an external local interface 130, such as a CRM device programmer, repeater, handheld device, and the like. The local interface 130 can be configured to communicate via a wired or wireless computer or communication network 132 to a remote interface 134, such as a remote computer, a server, and the like. In an example, the CRM device 100 is implanted within a subject. In an example, the CRM device 100 can include a non-invasive device that can be external to the subject. For example, the subject can wear the CRM device 100 as a patch, a strap, clothing, and the like.

The present systems or methods can be configured to enable diagnosis and management of cardiac arrhythmias or congestive heart failure ("CHF" or "heart failure"), among other physiological indications, for a patient with a heart disorder, via ongoing cardiac surveillance. The CRM device 100 can enable a physician to identify factors related to change in conductivity characteristics of a subject. The physician can receive prompt notification of urgent events as well as actionable information to diagnose symptomatic or asymptomatic physiological indications and proactively manage patients remotely from anywhere. In examples, the subject can also trigger on-demand collection of patient diagnostic data including, but not limited to, an electrocardiogram (ECG) upon experiencing symptoms, which can aid in the correlation of symptoms with the patient diagnostic data.

Figure 2:
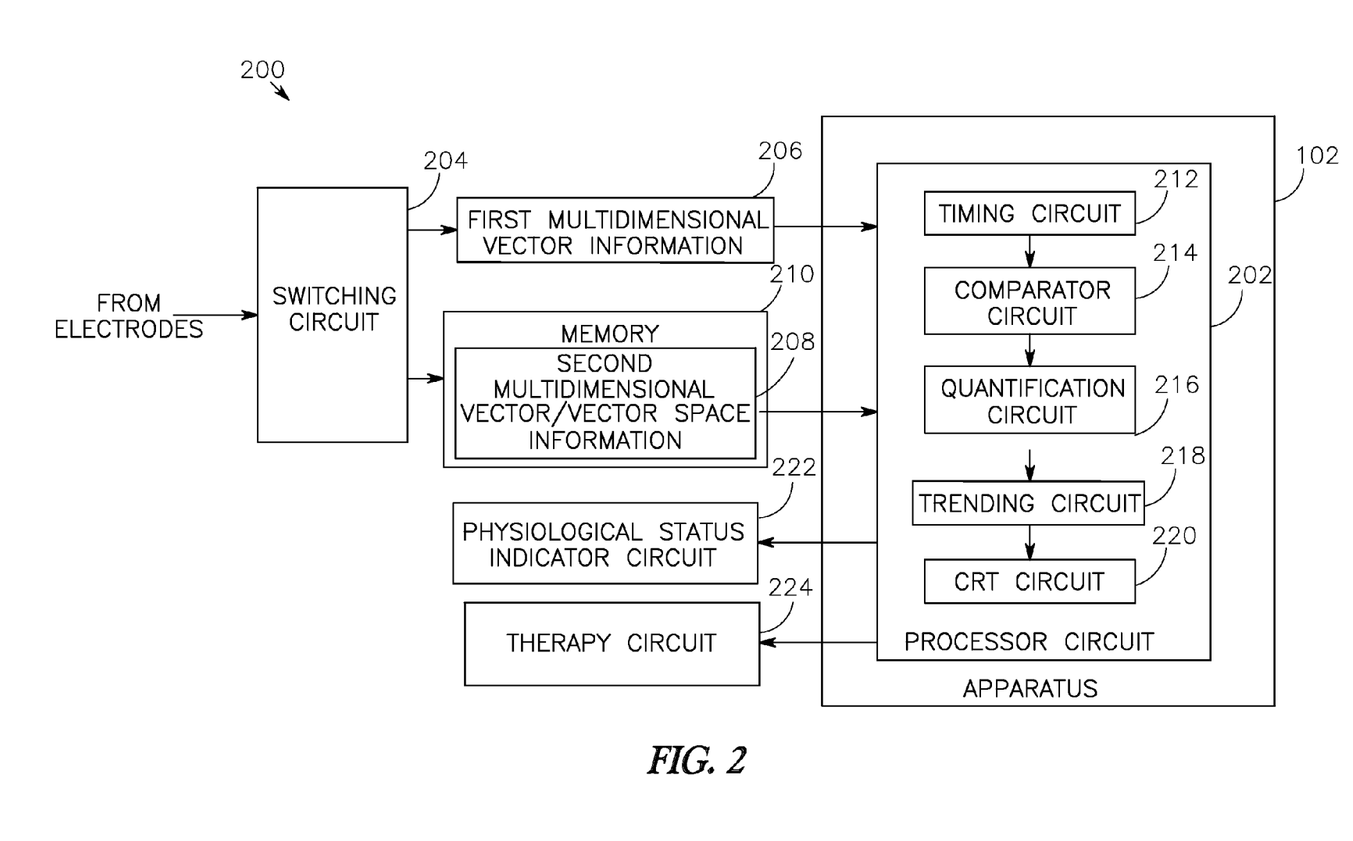
FIG. 2 illustrates, by way of an example but not by way of limitation, a block diagram depicting interaction of the implanted CRM device with other components.

FIG. 2 illustrates, by way of an example but not by way of limitation, a block diagram 200 that depicts interaction of the apparatus 102 with other components. The apparatus 102 can include a processor circuit 202. The processor circuit 202 can be configured to obtain a first multidimensional vector and a second multidimensional vector. In an example, the second multidimensional vector can be a multidimensional vector space. The first and second multidimensional vectors can be obtained by the processor circuit 202 through a switching circuit 204. The switching circuit 204 can selectively connect to various electrodes such as to leads 108A-108C. The switching circuit 204 can determine conductivity characteristics by switching between different electrode configurations to obtain the dimensions of the first multi-dimensional vector and the second multi-dimensional vector or space. In an example, the switching circuit 204 can include a switch array, a switch matrix, a multiplexer, or any other type of switching device suitable to selectively couple stimulation energy to selected electrodes. The switching circuit 204 can provide information 206 related to the first multidimensional vector (hereinafter referred to as first vector information 206). The first vector information 206 can include dimensions corresponding to respective first conductivity characteristics obtained from respective different implantable electrode configurations associated with a subject such as a patient.

In examples, the conductivity characteristics can include impedance, transimpedance, transconductance, or one or more others, such as measured using an electrode configuration. In an example, the first and second conductivity characteristics can include respective physiological impedances. In an example, the CRM device 100 can be configured to measure impedance along the different electrode configurations. Impedance can be measured by passing a specified current between a pair of electrodes (stimulating pair), measuring the resulting voltage between the same or different pair of electrodes (sensing pair), and using Ohm's law to compute resistance or impedance by dividing the sensed voltage with the stimulated current. In an example, the first and second conductivity characteristics can include respective changes in respective conductivity characteristic. The switching circuit 204 can provide information 208 related to the second multidimensional vector (hereinafter referred to as second vector information 208). In an example, the switching circuit 204 can provide second vector information 208 related to a multidimensional vector space. The second vector information 208 can include dimensions corresponding to respective second conductivity characteristics obtained from the different electrode configurations associated with the same or different subject. In examples, the second vector information 208 can include a template that is provided through an external interface. Further, the second vector information 208 can be stored in a memory 210 associated with the apparatus 102. The memory 210 can be configured to store the second conductivity characteristics obtained previously. In an example, a template of the second vector information 208 can be saved in the memory 210. The template can be used to combine and process first vector information 206 and second vector information 208 to determine physiological indications. The template can be fine-tuned for a subject, over a period of time, such that the template can be customized to the subject's consistent or stable physiological conditions. The template can be adjusted using physiological information about the same patient, such as can be obtained during patient maneuvers or using external laboratory measurements of the patient, either of which can be such as can be collected during hospitalization of the patient.

In examples, the different electrode configurations corresponding to respective dimensions of the first multidimensional vector can be the same as the different electrode configurations corresponding to the respective dimensions of the second multidimensional vector or vector space. In examples, the second multidimensional vector or vector space can be obtained earlier from the same subject or can be obtained from a patient population that can be representative of the same subject.

In examples, the processor circuit 202 can include a timing circuit 212, a comparator circuit 214, a quantification circuit 216, a trending circuit 218, and a Cardiac Resynchronization Therapy (CRT) control circuit 220. In examples, the CRT control circuit 220 is within the apparatus 102 or communicatively linked to the apparatus 102. The timing circuit 212 can perform functions that are related to scheduling, prompting, activating, or the like for various activities performed by the apparatus 102. The vector comparator circuit 214 can include a multidimensional vector comparator circuit that can be configured to compare the first multidimensional vector and the second multidimensional vector or vector space. Further, the quantification circuit 216 of the processor circuit 202 can generate an indication that is indicative of one or more risks based on the vector comparison. A risk could include a present or an expected abnormal physiological condition. In examples, the quantification circuit 216 can quantify data to identify one or more risks, or other indicators, associated with the subject based on the data. In an example, the one or more risks can include risks of pulmonary edema, heart failure, or the like. In another example, the quantification circuit 216 can detect the presence of a physiological condition such as detecting pulmonary edema specifically based on accumulation of fluid in lungs.

Further, the trending circuit 218 can be configured to provide a trend over a period of time. The trend can correspond to the vector comparisons done by the comparator circuit 214, such as including a trend of comparison results over a period of time. The CRT control circuit 220 can control delivery of CRT to co-ordinate spatial nature of heart depolarization such as for improving pumping efficiency such as for patients having Congestive Heart Failure (CHF.) The processor circuit 202 can provide or be associated with a physiological status indicator circuit 222 that can be configured to provide an indication of the vector comparison performed by the vector comparator circuit 214. As mentioned herein, the vector comparison can be of the first multidimensional vector and the second multidimensional vector or vector space. In an example, the processor circuit 202 can control, receive input from, or otherwise be associated with a therapy circuit 224. The therapy circuit 224 can be configured to adjust the delivery of electrical stimulation or other therapy to the subject based at least in part on the risk or other indicators identified by the quantification circuit 216.

Figure 3:
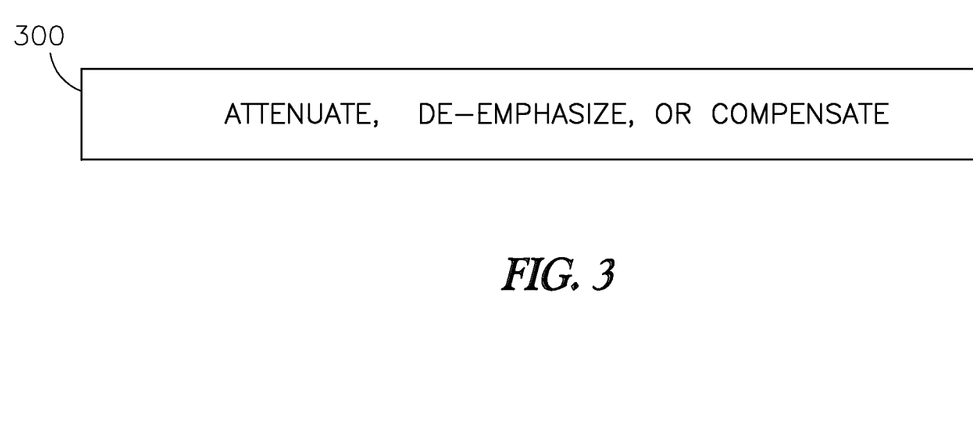
FIG. 3 illustrates, by way of an example but not by way of limitation, a chart of an example of processing variations in physiological conditions of a subject.

The processor circuit 202 can process the signals corresponding to the conductivity characteristics. The processing can be performed to improve signal quality to accurately determine variations in physiological conditions of a subject. FIG. 3 illustrates, by way of an example but not by way of limitation, a diagram 300 of an example of detecting or processing one or more variations in one or more physiological conditions of a subject. At 300, components of the signal corresponding to first and second conductivity characteristics can be attenuated or otherwise filtered. In examples, signal attenuation can be performed either before the vector comparison or as a part of the vector comparison. The attenuation can reduce components in the signal that are contributed by noise. For example, the components of signal contributed by the posture of a subject may be considered noise, and therefore can be attenuated from the signal as it may swamp or affect another physiological signal of interest. For example, a 3-axis accelerometer can be configured as a posture sensor, and signal components from this sensor could be processed to disregard physiological data gathered when the subject is in a particular posture, or undergoing a particular posture change. In examples, the component of signals contributed by the posture may be of interest, and other components contributed by other physiological factors can be attenuated. Posture information can be additionally or alternatively indirectly inferred from a proxy, such as using time-of-day information to infer when the patient is likely upright (e.g., during the day) or when the patient is likely not upright (e.g., during the nighttime). In addition or alternative to attenuation, the noise components can be de-emphasized, such as by gating the signal to remove time periods associated with the presence of noise. In addition or alternative to attenuation or de-emphasis, the noise components of the signal can be compensated for (e.g., using automatic gain control (AGC) or another compensation technique), such as to accommodate variation in factors such as a circadian or other biologic rhythm variation, a cardiac cycle, a respiration cycle, a physical activity, a posture, or the like of the subject. In an example, physical activity may in certain instances be a confounding variable. In this example, a sensor can detect the subject's physical activity. A sensing circuit that can be coupled to the processor circuit 202 can sense these factors. The processor circuit 202 can perform the multi-vector comparison at like-physical activity levels. For example, the multi-vector comparison can be performed only while the subject is at rest. In examples, the variations contributed by different physical activities can be attenuated, de-emphasized, or compensated to perform the vector comparison by the comparator circuit 214. In an example, the processing circuit 202 can be configured to attenuate, de-emphasize, or compensate the variations.

Figure 4:
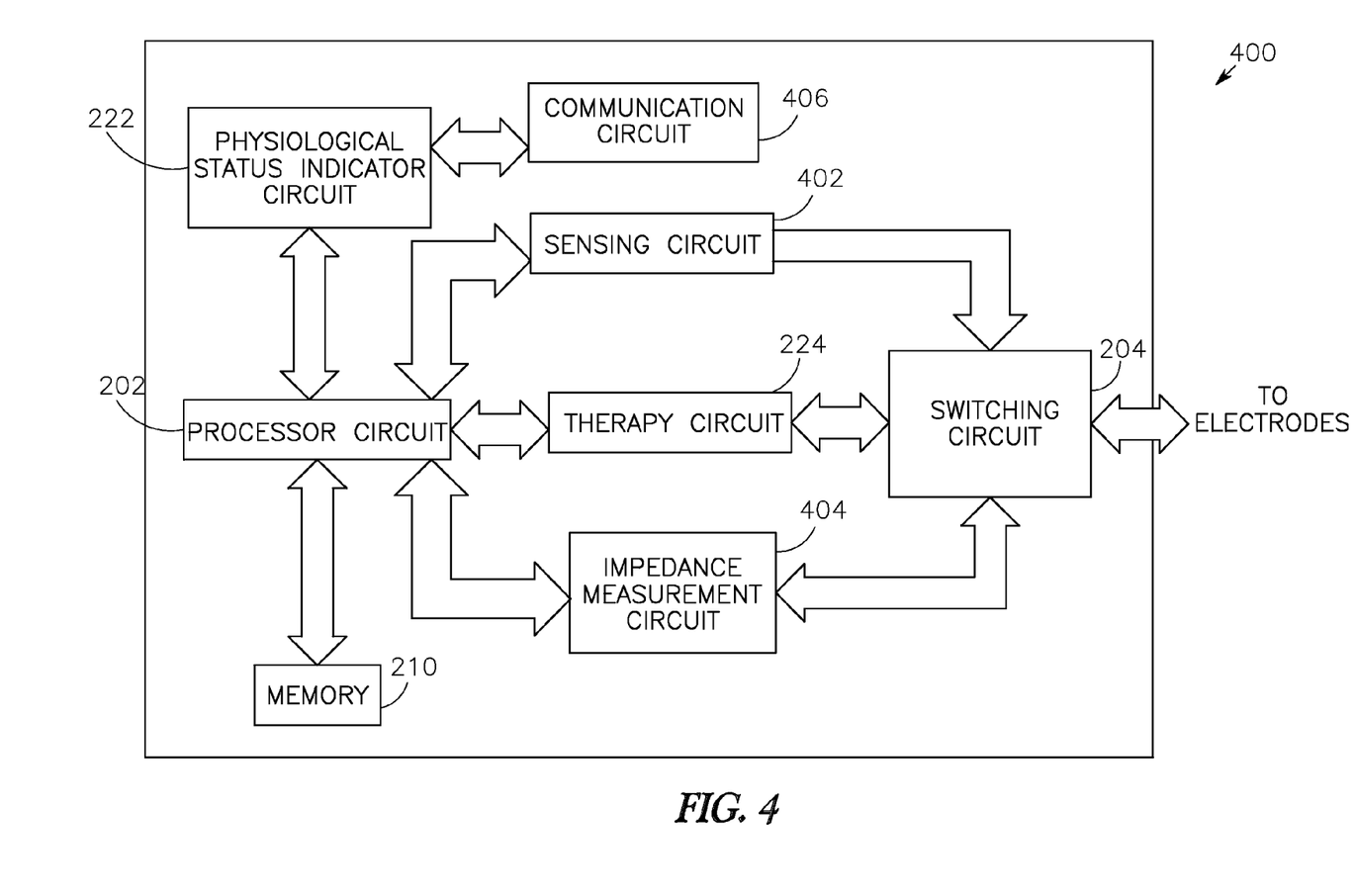
FIG. 4 illustrates, by way of an example but not by way of limitation, an example of a processor circuit in communication with various other circuits.

FIG. 4 illustrates, by way of an example but not by way of limitation, an example of the processor circuit 202 in communication with various other circuits. As mentioned above, the processor circuit 202 can communicate with the switching circuit 204 for selectively connecting various electrodes. Further, a sensing circuit 402 can be selectively coupled to various electrodes by the switching circuit 204. The sensing circuit 402 can include one or any combination of one or more sense amplifiers, one or more filter circuits, or one or more other circuits such as for sensing one or more intrinsic electrical signals or one or more other physiological signals. In an example, the sensing circuit 402 can include a cardiac sensor, a posture sensor, a respiration sensor, a physical activity sensor, and the like. In an example, the processor circuit 202 can be configured to obtain a first posture indicator providing a posture indicator associated with the first multidimensional vector. The posture sensor of the sensing circuit 402 can provide the first posture indicator to the processor circuit 202. The first posture indicator can be used to select the second multidimensional vector space or vector from a plurality of second multidimensional vector spaces or vectors associated with different postures. The second multidimensional vector space or vector can provide information associated with a like posture to that provided by the posture indicator associated with the first multidimensional vector.

Thereafter, the physiological status indication can be obtained at least in part by performing a like-posture vector comparison of the first multidimensional vector to the second multidimensional vector space or vector. The like-posture vector comparison can refer to a vector comparison done between conductivity characteristics of two or more vectors when the subject is in a similar posture while obtaining readings for the two or more vectors. In an example, at least one of these two vectors can be a template vector, and at least one other of these vectors can include substantially real-time or other ongoing acquired or trended physiological data, which can undergo a multidimensional vector comparison to the at least one template vector.

A therapy circuit 224 can be selectively coupled to selected electrodes through the switching circuit 204 and can include therapy energy generation circuit such as for generating, storing, or delivering one or more of an electrostimulation, cardioversion, defibrillation, or other energy or therapeutic agent delivery or other therapy. In examples, the processor circuit 202 can be configured to determine the therapy titration or other control signal at least in part by using the physiological status indication obtained at least in part by performing a vector comparison of the first multidimensional vector to the second multidimensional vector or vector space. Further, an impedance (or other conductivity characteristic) measurement circuit 404 can be selectively coupled to selected electrodes such as through the switching circuit 204. For example, the impedance measurement circuit 404 can be used for measuring lead impedance, a tissue impedance, a regional or organ impedance, or other conductivity characteristic.

As indicated in FIG. 4, the sensing circuit 402, the therapy circuit 224, and the impedance measurement circuit 404 can be coupled to the processor circuit 202. In an example, the processor circuit 202 can perform one or more instructions, such as for signal processing of one or more signals that can be derived by the sensing circuit 402 or the impedance measurement circuit 404. In an example, the processor circuit 202 can perform one or more instructions such as for controlling operation of the therapy circuit 224. In an example, the processor circuit 202 can include or be coupled to the memory 210. The memory 210 can be configured to store or retrieve information. Such information can include dimensions corresponding to respective conductivity characteristics of the subject. The processor circuit 202 can be coupled to the physiological status indicator circuit 222 such as for providing one or more indications or one or more alerts, such as based on the input received from one or more other circuits such as the sensing circuit 402, the impedance measurement circuit 404, or other circuit. In examples, the physiological status indicator circuit 222 can be coupled to a communication circuit 406, such as for communicating with a local interface 130.

The physiological status indicator circuit 222 can be configured to detect a first physiological condition as distinguishable from at least one second physiological condition. The first and the second physiological conditions can be both capable of affecting one or more physiological impedances. In an example, the first and the second physiological conditions can include any two of a vascular volume status, a vascular engorgement status, a hematocrit status, a blood conductivity or resistivity status, an extravascular lung volume status, an Implantable Medical Device (IMD) pocket fluid status, or the like.

In an example, one or more indications can be obtained at least in part by the physiological status indicator circuit 222 such as by performing a static or dynamic vector comparison of the first multidimensional vector to the second multidimensional vector or vector space. The static vector comparison can correspond to comparison of the first multidimensional vector to the second multidimensional vector or vector space at a particular time. Dynamic vector comparison can correspond to multiple comparisons of the first multidimensional vectors to the second multidimensional vectors or vector spaces over a period of time. In examples, the one or more indications can indicate congestive heart failure (CHF) compensation or decompensation status of the subject. In an example, a trajectory of the first multidimensional vector with respect to the second multidimensional vector or vector space can be used to provide the physiological status indication. In examples, the trajectory can be the path traced by the first multidimensional vector with respect to the second multidimensional vector over a period of time. In examples, the trajectory can be of the relative position of the first multidimensional vector with respect to the second multidimensional vector or vector space. In an example, the trajectory can be of proximity of the first multidimensional vector to the second multidimensional vector or vector space. The processor circuit 202 can be configured to provide the physiological status indication to a user or an automated process.

Figure 5:
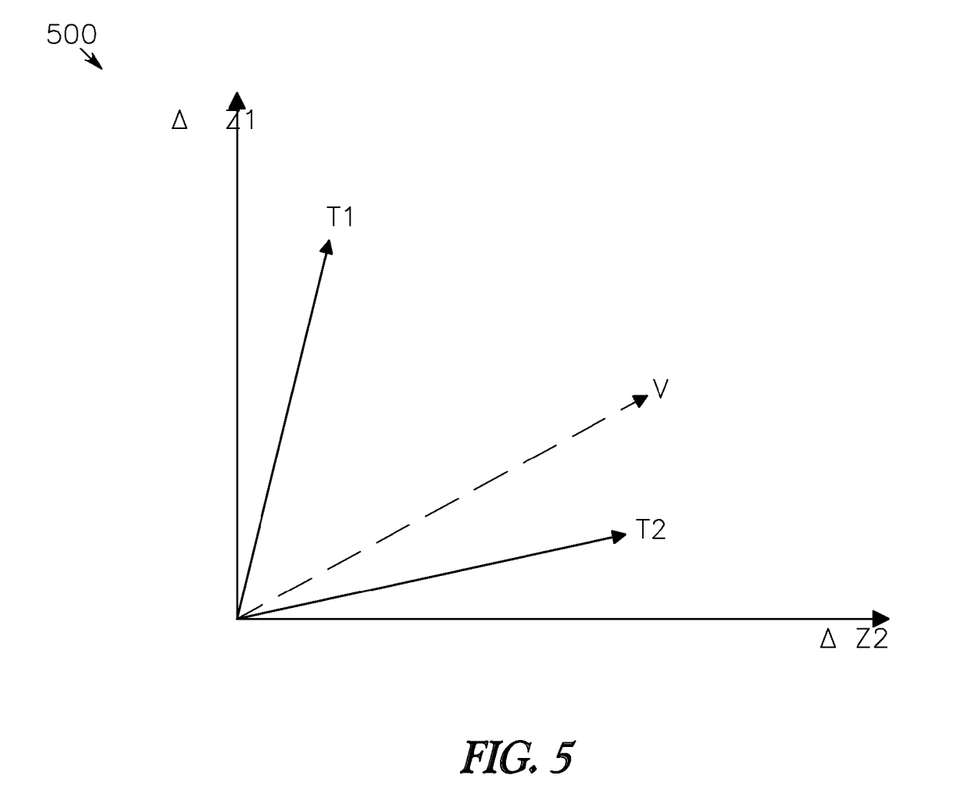
FIG. 5 illustrates, by way of an example but not by way of limitation, a graph illustrating examples of experimentally-observed data of proximity between a first multidimensional vector and a second multidimensional vector or vector space.

FIG. 5 illustrates, by way of an example but not by way of limitation, a graph 500 illustrating conceptual examples of data of proximity between a first multidimensional vector and a second multidimensional vector space or vector. As explained herein, the processor circuit 202 can be configured to provide the multidimensional physiological status indicator, which can be obtained at least in part by performing a static or dynamic vector comparison. The comparison can be performed between the first vector information 206 and the second vector information 208. In an example, the first and second multidimensional vectors can be represented in a multidimensional space. In an example, an individual axis of the multidimensional space can represent a conductivity characteristic, such as impedance, along one of the electrode configurations. The second multidimensional vector or vector space can include a plurality of unit vectors that can be identified in the multidimensional space. The individual unit vectors can correspond to respective clinically relevant factors that can affect the impedance or other conductivity characteristic.

In an example, such as shown in FIG. 5, T1 can reflect a first template representing lung water of a subject and T2 can represent a second template representing vascular volume change of the subject. Together, T1 and T2 represent the second multi-dimensional vector or vector space. In an example, a change in impedance can be evaluated, such as represented in FIG. 5 as the first multidimensional vector V. Proximity of the impedance vector V to the unit vectors T1 and T2 can be considered as a basis for evaluating the likelihood of various clinical factors that can contribute to the observed impedance change. Accordingly, the multidimensional physiological status can be obtained and provided to the user or the automated process by the processor circuit 202. The multidimensional physiological status indicator can include dimensions that can correspond to one or more respective factors representing one or more respective contributions associated with one or more different physiological conditions.

In an example, the processor circuit 202 can be configured to measure a "distance" such as between the end-point of a first multidimensional vector V1 and the end-point of a second multidimensional vector V2. The distance can be measured by taking a Root Mean Square (RMS) of a difference of the first multidimensional vector and the second multidimensional vector, i.e., $|V_1-V_2|$. In an example, a projection of the first multidimensional vector V1 on the second multidimensional vector V2 can be taken. This can also be referred to as an inner product ($V_1^T V_2$). Another metric for vector comparison can be an angle between the two vectors V1 and V2. A cosine of this angle is mathematically the inner product of unit vectors along the two vectors.

As explained herein, the processor circuit 202 can be configured to adjust the multidimensional physiological status indicator, such as to account for relative risks associated with respective different physiological conditions. For example, a change in one or more particular physiological conditions (such as extravascular lung water, for example) can be more severe than a change in one or more other particular physiological conditions. In an example, a physiological condition can be classified one of multiple risk strata. In examples, the risk can prompt a clinician to prescribe new, different, or additional therapy, such as to adjust the existing therapy, such as one or more parameters associated with cardiac electrical stimulation therapy or dosages associated with a drug.

In an example, the processor circuit 202 can be configured to provide a trend of at least one of the first multidimensional vector or the first physiological status indicator that was obtained at least in part by performing a vector comparison of the first multidimensional vector to the second multidimensional vector space or vector. The trend can be determined within a certain period of time. In an example, the trend can be determined within an hour or over a time period that is longer than an hour. The trend can illustrate the proximity of the impedance vector V to the unit vectors T1 and T2. The trend can be provided by recurrently or periodically tracking the impedance vector V in the multidimensional space. Based on the trend, one or more alerts can be generated that can be indicative of a need for automated, semi-automated, or human-provided intervention. For example, the processor circuit 202 can be programmed or otherwise configured to respond to a detected pocket fluid condition by initiating or altering a therapy or triggering an alert to generate an alert signal to the subject or the physician about a serious or other condition that can justify medical intervention.

In examples, the second multidimensional vector or vector space can be obtained from an initial template such as can be obtained from a patient population that can be representative (e.g., similar age, gender, etc.) of the particular subject. The initial template can be adjusted as per the particular subject by using physiological information about the particular subject. The physiological information can be obtained by tracking one or more physiological conditions of the subject over time. The memory 210 can include a generic initial template of the second multidimensional vector or vector space. This generic template can be customized such as per the subject's one or more particular physiological conditions.

Figure 6:
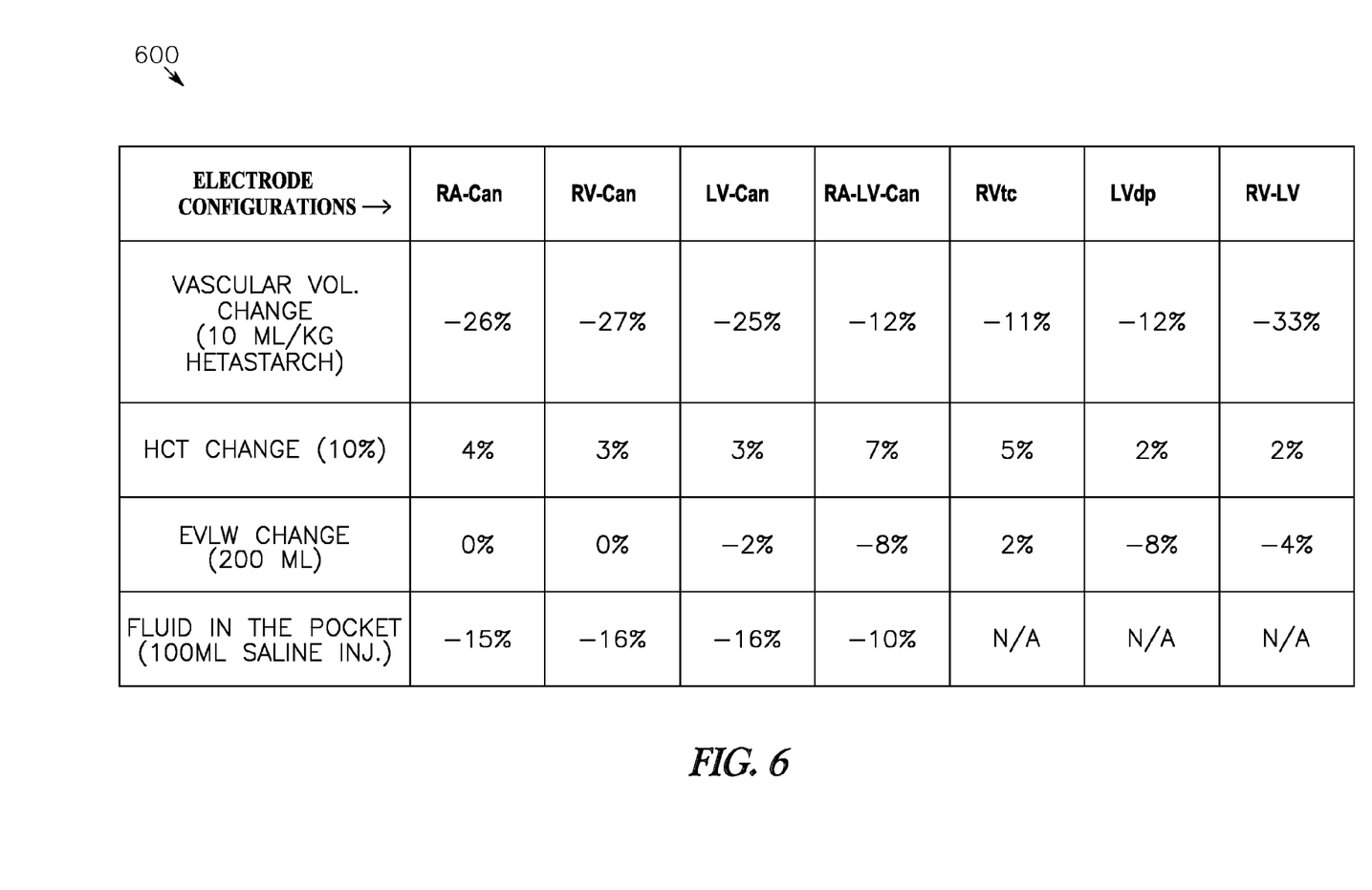
FIG. 6 illustrates, by way of an example but not by way of limitation, a table depicting susceptibility of a plurality of vectors to changes in impedances in a plurality of physiological factors.

FIG. 6 illustrates, by way of an example but not by way of limitation, a table 600 depicting an example of susceptibility of a plurality of electrode configurations to changes in impedances that can involve a plurality of physiological factors. In an example, the plurality of physiological factors can include vascular volume change, hematocrit change, extravascular lung water status, pocket fluid status, and the like. The dimensions in the multi-dimensional vectors provided by the electrode configurations, as indicated by an arrow, can include test energy delivery electrodes or test energy delivery response sensing electrodes. For example, a dimension RA-Can can refer to test energy delivery or test energy delivery response sensing between the at least one electrode located at the right atrium and at least one electrode located at the can. The 'Can' can be an electrode that is located either at the housing 104 or at the header 106 of the electronics unit of the implantable CRM device 100. Similarly, RV-Can and LV-Can can respectively refer to stimulation and sensing between the RV and Can and the LV and Can. Similarly, RA-LV-Can can refer to stimulation and sensing between the RA, and LV and Can jointly. The table 600 also depicts an example of the possible effect of change in the impedances of the plurality of physiological states on the vectors. For example, the vector RV-Can can be more sensitive to changes in the vascular volume as compared to other physiological factors. The vector RA-LV-Can can be less sensitive to changes in vascular volume than the vector RV-Can. Further, the vector RA-LV-Can can be more sensitive to changes in extra-vascular lung water status as compared to one or more other vectors.

A device-readable medium can also be provided. The device-readable medium can include one or more device-readable instructions that, when performed by the device, can cause the device to perform an act of obtaining a first multidimensional vector. The first multidimensional vector can include dimensions corresponding to the respective first conductivity characteristics obtained from different electrode configurations associated with a subject. The device can also perform the act of obtaining a second multidimensional vector space or vector. The second multidimensional vector space or vector can include dimensions corresponding to respective second conductivity characteristics obtained from the different electrode configurations associated with the same or a different subject. The first conductivity characteristics can be of the same type as the second conductivity characteristics. For example, corresponding dimensions of the first multidimensional vector and the second multidimensional vector or vector space can include conductivity characteristics that were obtained using the same electrode configuration. In an example, the first and the second conductivity characteristics can include physiological impedances, or changes in respective physiological impedances.

In an example, the different electrode configurations corresponding to the respective dimensions of the first multidimensional vector can be of the same type as the different electrode configurations corresponding to the respective dimensions of the second multidimensional vector space or vector. The device can perform the act of providing a physiological status indicator obtained at least in part by performing a vector comparison of the first multidimensional vector to the second multidimensional vector space or vector. The physiological impedances can be affected by variation in a cardiac cycle, a respiration cycle, a physical activity, a posture, a cough or other respiration artifact, or the like of the subject. These variations can be attenuated, de-emphasized, or compensated for performing the vector comparison.

In an example, the device can obtain the second multidimensional vector space or vector earlier from the same subject or from a patient population that can be representative of the same subject. The device can provide the physiological status indicator to detect a first physiological condition as distinguishable from at least one second physiological condition. The first and second physiological conditions can be capable of affecting the physiological impedances.

In examples, the device can be configured to obtain a first posture indicator that can provide a posture indication associated with the first multidimensional vector. As explained herein, the posture sensor of the sensing circuit 402 (FIG. 4) can provide the first posture indicator. The first posture indicator can be used to select the second multidimensional vector space or vector from a plurality of second multidimensional vector spaces or vectors associated with different postures. The second multidimensional vector space or vector can provide information associated with a like posture to the posture indicator associated with the first multidimensional vector. The physiological status indicator can be obtained at least in part by performing a like-posture vector comparison of the first multidimensional vector to the second multidimensional vector space or vector.

In examples, the device can be configured to provide a multidimensional physiological status indicator that can be obtained at least in part by performing a regression or like vector comparison of the first multidimensional vector to the second multidimensional vector space or vector. A statistical analysis technique, such as regression, can determine the influence of one multidimensional vector on another multidimensional vector. Such a comparison can provide accurate indication of the contribution of at least one particular physiological condition in the change of impedance. In examples, the part of the first multidimensional vector that is un-explainable by the second multi-dimensional vector or vector space may be separately reported or trended as an "unknown clinical cause". The multidimensional physiological status indicator can include dimensions corresponding to factors representing contributions associated with different physiological conditions. The device can further be configured to adjust the multidimensional physiological status indicator to account for relative risks associated with different physiological conditions.

Figure 7:
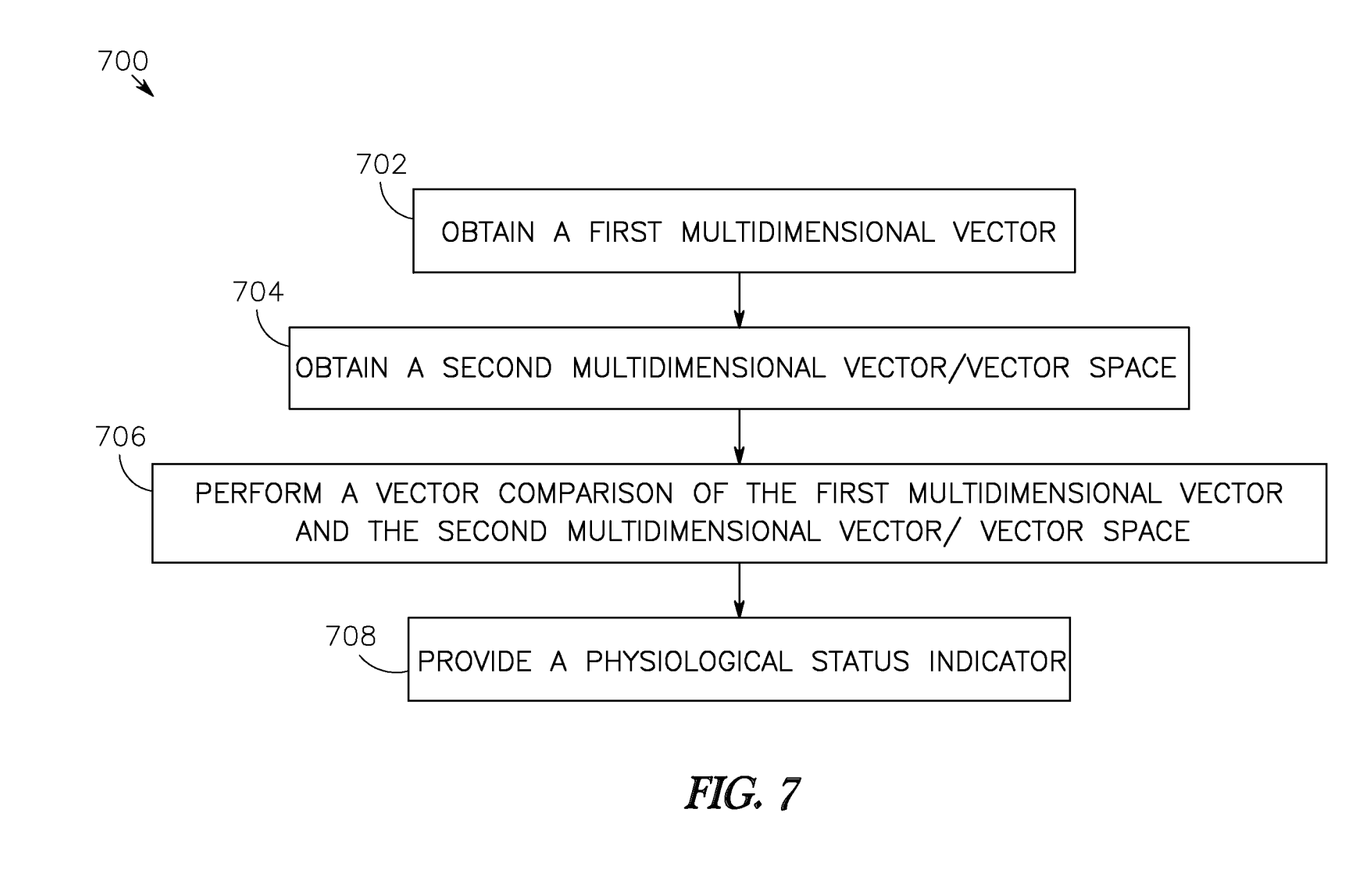
FIG. 7 illustrates, by way of an example but not by way of limitation, a chart depicting a method for providing a physiological status indicator.

FIG. 7 illustrates, by way of an example but not by way of limitation, a diagram depicting a method 700 for providing a physiological status indicator. The method 700 can be performed by the apparatus 102 and will be explained in conjunction with FIGS. 2 and 4. At 702, a first multidimensional vector can be obtained. The first multidimensional vector can include dimensions corresponding to the respective first conductivity characteristics obtained from different implantable electrode configurations associated with a subject. At 704, a second multidimensional vector or vector space can be obtained. The second multidimensional vector or vector space can include dimensions corresponding to the respective second conductivity characteristics obtained from the different electrode configurations associated with the same or different subject. The first conductivity characteristics can be of the same type as the second conductivity characteristics. Further, the different electrode configurations corresponding to the respective dimensions of the first multidimensional vector can be of the same type as the different electrode configurations corresponding to the respective dimensions of the second multidimensional vector space or vector.

At 706, a vector comparison of the first multidimensional vector to the second multidimensional vector space or vector can be performed. The vector comparison can be a static or dynamic comparison. The vector comparison can be used for providing a physiological status indicator, as shown at 708. The processor circuit 202 of the apparatus 102 can be configured to perform the above.

Figure 8:
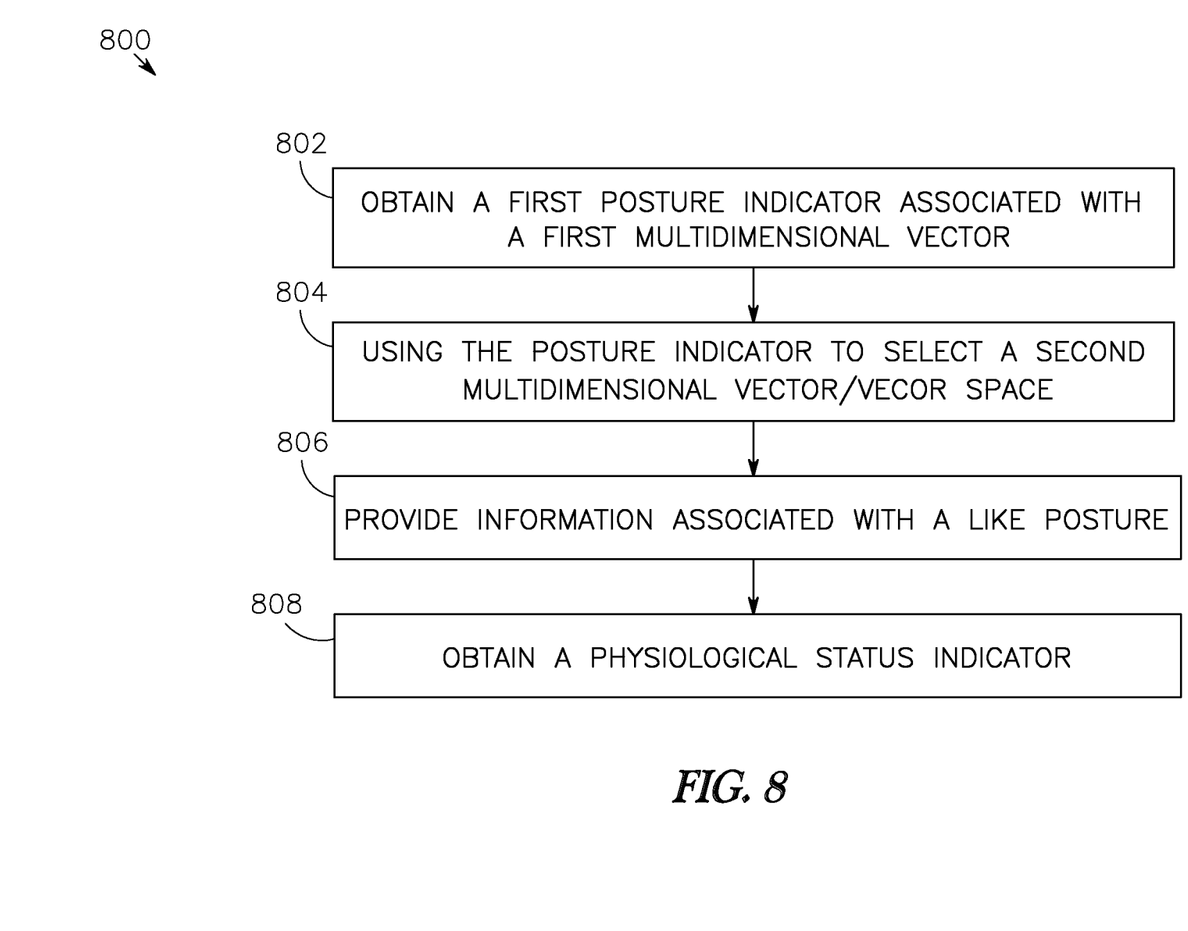
FIG. 8 illustrates, by way of an example but not by way of limitation, a chart depicting a method for providing a physiological status indicator based on a posture of a subject.

FIG. 8 illustrates, by way of an example but not by way of limitation, a diagram depicting a method 800 for providing a physiological status indicator based on a posture of the subject. In examples, the method 800 de-emphasizes postural variation during vector comparison. At 802, a first posture indicator provides a posture indicator associated with the first multidimensional vector. At 804, the first posture indicator can be used to select the second multidimensional vector or vector space. The second multidimensional vector or vector space can be selected from a plurality of second multidimensional vector spaces or vectors associated with different postures. Further, at 806, information associated with a like posture can be provided to the posture indicator associated with the first multidimensional vector. At 808, a like-posture vector comparison of the first multidimensional vector to the second multidimensional vector or vector space can be performed to obtain a physiological status indicator at least in part.

Figure 9:
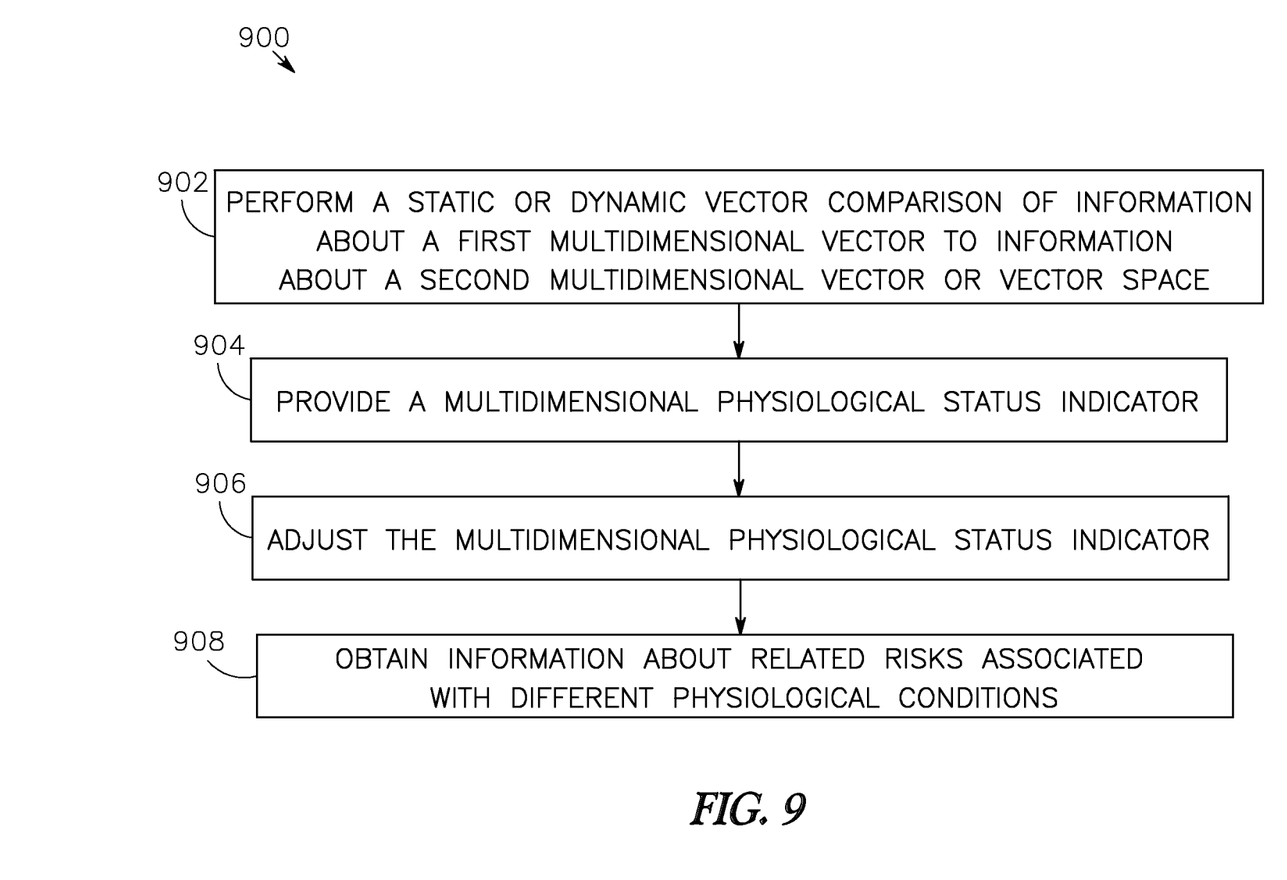
FIG. 9 illustrates, by way of an example but not by way of limitation, a chart depicting a method for obtaining information about related risks associated with different physiological conditions of the subject.

Referring to FIG. 9, a diagram depicts, by way of an example but not by way of limitation, a method 900 for obtaining information about related risks associated with different physiological conditions of the subject. At 902, a static or dynamic vector comparison can be performed at least in part of information about a first multidimensional vector to information about a second multidimensional vector space or vector. At 904, the static or dynamic vector comparison can provide a multidimensional physiological status indicator. The multidimensional physiological status indicator can include dimensions that can correspond to factors representing contributions associated with different physiological conditions such as blood resistivity, lung resistivity, posture of a subject, physical activity of the subject, heart muscle resistivity, or others. At 906, the multidimensional physiological status indicator can be adjusted. The adjustment can account for relative risks associated with different physiological conditions at 908.

Each of these non-limiting examples can stand on its own, or can be combined in any permutation or combination with any one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b),

What is claimed is:

1. An apparatus comprising:
   a processor circuit, configured to
   obtain a first multidimensional vector, comprising dimensions corresponding to respective first conductivity characteristics obtained from different implantable electrode configurations associated with a subject;
   obtain a second multidimensional vector space or vector, comprising dimensions corresponding to respective second conductivity characteristics obtained from the different electrode configurations associated with the same or a different subject, wherein the first conductivity characteristics are of the same type as the second conductivity characteristics, and wherein the different electrode configurations corresponding to the respective dimensions of the first multidimensional vector are of the same type as the different electrode configurations corresponding to the respective dimensions of the second multidimensional vector space or vector; and
   providing a physiological status indicator obtained at least in part by performing a vector comparison that determines proximity of the first multidimensional vector to the second multidimensional vector space or vector.

2. The apparatus of claim 1, wherein the processor circuit is configured such that:
   the first conductivity characteristics and the second conductivity characteristics comprise physiological impedances, or changes in respective physiological impedances, in which at least one of circadian or other biological rhythm variations, cardiac cycle variations, respiration cycle variations, physical activity variations, or posture variations are attenuated, de-emphasized, or compensated for performing the vector comparison;
   the second multidimensional vector space or vector is obtained earlier from the same subject or obtained from a patient population that is representative of the same subject; and
   the physiological status indicator is configured to detect a first physiological condition as distinguishable from at least one second physiological condition, wherein the first and second physiological conditions are both capable of affecting the physiological impedances.

3. The apparatus of claim 2, wherein the first and second physiological conditions include any two of the following: (1) vascular volume status; (2) vascular engorgement status; (3) hematocrit status; (4) blood conductivity status (5) extravascular lung water status; and (6) implantable medical device (IMD) pocket fluid status.

4. The apparatus of claim 1, wherein the physiological status indicator obtained at least in part by performing a static or dynamic vector comparison of the first multidimensional vector to the second multidimensional vector space or vector indicates congestive heart failure (CHF) compensation or decompensation status, and wherein the processor circuit is configured to provide the physiological status indicator to a user or to an automated process.

5. The apparatus of claim 1, wherein the processor circuit is configured to provide a therapy titration control signal, and wherein the processor circuit is configured to determine the therapy titration control signal at least in part using the physiological status indicator obtained at least in part by performing the vector comparison of the first multidimensional vector to the second multidimensional vector space or vector.

6. The apparatus of claim 1, wherein the processor circuit is configured to
   obtain a first posture or time-of-day indicator providing a posture or time-of-day indicator associated with the first multidimensional vector;
   use the first posture or time-of-day indicator to select the second multidimensional vector space or vector, from a plurality of second multidimensional vector spaces or vectors associated with different postures or times-of-day, to provide information associated with a like posture or time-of-day to the posture or time-of-day indicator associated with the first multidimensional vector; and
   wherein the physiological status indicator is obtained at least in part by performing a like-posture or like time-of-day vector comparison of the first multidimensional vector to the second multidimensional vector space or vector.

7. The apparatus of claim 1, wherein the processor circuit is configured to provide a multidimensional physiological status indicator obtained at least in part by performing a static or dynamic vector comparison of information about the first multidimensional vector to information about the second multidimensional vector space or vector, wherein the multidimensional physiological status indicator includes dimensions corresponding to factors representing contributions associated with different physiological conditions.

8. The apparatus of claim 7, wherein the processor circuit is configured to adjust the multidimensional physiological status indicator to account for relative risks associated with the different physiological conditions.

9. The apparatus of claim 1, wherein the processor circuit is configured to provide a trend, over a period of time that is longer than at least one hour, of at least one of: (1) the first multidimensional vector or (2) the physiological status indicator obtained at least in part by performing the vector comparison of the first multidimensional vector to the second multidimensional vector space or vector.

10. The apparatus of claim 1, wherein the second multidimensional vector space or vector is obtained from an initial template obtained from a patient population that is representative of the same subject, wherein the initial template is adjusted using physiological information about the same subject.

11. A non-transitory device-readable medium including device-readable instructions that, when performed by a device, cause the device to perform the following acts:
    obtaining a first multidimensional vector, comprising dimensions corresponding to respective first conductivity characteristics obtained from different electrode configurations associated with a subject;
    obtaining a second multidimensional vector space or vector, comprising dimensions corresponding to respective second conductivity characteristics obtained from the different electrode configurations associated with the same or a different subject, wherein the first conductivity characteristics are of the same type as the second conductivity characteristics, and wherein the different electrode configurations corresponding to the respective dimensions of the first multidimensional vector are of the same type as the different electrode configurations corresponding to the respective dimensions of the second multidimensional vector space or vector; and providing a physiological status indicator obtained at least in part by performing a vector comparison of the first multidimensional vector to the second multidimensional vector space or vector, wherein the performing the vector comparison includes determining proximity of the first multidimensional vector to the second multidimensional vector space or vector.

12. The device-readable medium of claim 11, including device-readable instructions that, when performed by the device, cause the device to perform the following acts:

obtaining the first multidimensional vector and obtaining the second multidimensional vector space or vector, such that the first conductivity characteristics and the second conductivity characteristics comprise physiological impedances, or changes in respective physiological impedances, in which at least one of circadian or other biological rhythm variations, cardiac cycle variations, respiration cycle variations, physical activity variations, or posture variations are attenuated, de-emphasized, or compensated for performing the vector comparison;

obtaining the second multidimensional vector space or vector earlier from the same subject or from a patient population that is representative of the same subject; and providing the physiological status indicator to detect a first physiological condition as distinguishable from at least one second physiological condition, wherein the first and second physiological conditions are both capable of affecting the physiological impedances.

13. The device-readable medium of claim 11, including device-readable instructions that, when performed by the device, cause the device to perform the following acts:

obtaining a first posture or time-of-day indicator providing a posture or time-of-day indicator associated with the first multidimensional vector;

using the first posture or time-of-day indicator to select the second multidimensional vector space or vector, from a plurality of second multidimensional vector spaces or vectors associated with different postures or times-of-day, to provide information associated with a like posture or like-time-of-day to the posture or time-of-day indicator associated with the first multidimensional vector; and wherein the physiological status indicator is obtained at least in part by performing a like-posture or like-time-of-day vector comparison of the first multidimensional vector to the second multidimensional vector space or vector.

14. The device-readable medium of claim 11, including device-readable instructions that, when performed by the device, cause the device to perform the following act:

providing a multidimensional physiological status indicator obtained at least in part by performing a regression or like vector comparison of the first multidimensional vector to the second multidimensional vector space or vector, wherein the multidimensional physiological status indicator includes dimensions corresponding to factors representing contributions associated with different physiological conditions.

15. The device-readable medium of claim 14, including device-readable instructions that, when performed by the device, cause the device to perform the following act:

adjusting the multidimensional physiological status indicator to account for relative risks associated with the different physiological conditions.

16. A method performed by an apparatus, the method comprising:

obtaining a first multidimensional vector, comprising dimensions corresponding to respective first conductivity characteristics obtained from different implantable electrode configurations associated with a subject;

obtaining a second multidimensional vector space or vector, comprising dimensions corresponding to respective second conductivity characteristics obtained from the different electrode configurations associated with the same or a different subject, wherein the first conductivity characteristics are of the same type as the second conductivity characteristics, and wherein the different electrode configurations corresponding to the respective dimensions of the first multidimensional vector are of the same type as the different electrode configurations corresponding to the respective dimensions of the second multidimensional vector space or vector; and providing a physiological status indicator obtained at least in part by performing a static or dynamic vector comparison of the first multidimensional vector to the second multidimensional vector space or vector, wherein the performing the static or dynamic vector comparison includes determining proximity of the first multidimensional vector to the second multidimensional vector space or vector.

17. The method of claim 16, comprising:

obtaining the first multidimensional vector and obtaining the second multidimensional vector space or vector, such that the first conductivity characteristics and the second conductivity characteristics comprise physiological impedances, or changes in respective physiological impedances, in which at least one of circadian or other biological rhythm variations, cardiac cycle variations, respiration cycle variations, physical activity variations, or posture variations are attenuated, de-emphasized, or compensated for performing the vector comparison;

obtaining the second multidimensional vector space or vector earlier from the same subject or from a patient population that is representative of the same subject; and providing the physiological status indicator to detect a first physiological condition as distinguishable from at least one second physiological condition, wherein the first and second physiological conditions are both capable of affecting the physiological impedances.

18. The method of claim 16, comprising:

obtaining a first posture or time-of-day indicator providing a posture or time-of-day indicator associated with the first multidimensional vector;

using the first posture or time-of-day indicator to select the second multidimensional vector space or vector, from a plurality of second multidimensional vector spaces or vectors associated with different postures or times-of-day, to provide information associated with a like posture or like-time-of-day to the posture or time-of-day indicator associated with the first multidimensional vector; and wherein the physiological status indicator is obtained at least in part by performing a like-posture or like-time-of-day vector comparison of the first multidimensional vector to the second multidimensional vector space or vector.

19. The method of claim 16, comprising:

providing a multidimensional physiological status indicator obtained at least in part by performing the static or dynamic vector comparison of information about the first multidimensional vector to information about the second multidimensional vector space or vector, wherein the multidimensional physiological status indicator includes dimensions corresponding to factors representing contributions associated with different physiological conditions.

20. The method of claim 19, comprising:

adjusting the multidimensional physiological status indicator to account for relative risks associated with the different physiological conditions.

* * * * *